United States Patent
Fonknechten et al.

(10) Patent No.: US 7,182,960 B2
(45) Date of Patent: Feb. 27, 2007

(54) PHARMACEUTICAL COMPOSITIONS FOR NASAL DELIVERY OF OESTRADIOL AND NORETHISTERONE

(75) Inventors: Gilles Fonknechten, Orleans (FR); Patrick Wuthrich, Orleans (FR); Yannis Tsouderos, Paris (FR); Claire Varin, Le Vesinet (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 304 days.

(21) Appl. No.: 10/483,551

(22) PCT Filed: Jul. 18, 2002

(86) PCT No.: PCT/FR02/02561

§ 371 (c)(1), (2), (4) Date: Jan. 12, 2004

(87) PCT Pub. No.: WO03/015751

PCT Pub. Date: Feb. 27, 2003

(65) Prior Publication Data

US 2004/0180856 A1 Sep. 16, 2004

(30) Foreign Application Priority Data

Jul. 19, 2001 (FR) .................... 01 09654

(51) Int. Cl.
*A61K 9/08* (2006.01)
*A61K 31/56* (2006.01)

(52) U.S. Cl. ............ 424/488; 514/177; 514/178; 514/182

(58) Field of Classification Search ......... 514/182, 514/177, 178; 424/488
See application file for complete search history.

(56) References Cited

U.S. PATENT DOCUMENTS

| 5,514,673 A | * | 5/1996 | Heckenmuller et al. .... 514/177 |
| 5,759,573 A | * | 6/1998 | Kim ............................ 424/450 |
| 5,955,454 A | * | 9/1999 | Merkus ...................... 514/177 |
| 2002/0150616 A1 | * | 10/2002 | Vandecruys ................ 424/464 |

FOREIGN PATENT DOCUMENTS

| EP | 0349091 | | 1/1990 |
| WO | WO 94/22461 | * | 10/1994 |
| WO | WO 00/21503 | * | 4/2000 |

OTHER PUBLICATIONS

*Search Report* for French National Application 01/09654, filed Jul. 19, 2001, two (2) pages.
Kublik, et al. 1996, Eur. J. Pharm. Biopharm. 42(5):320-324.

* cited by examiner

*Primary Examiner*—Johann R. Ricther
*Assistant Examiner*—James Henry Alstrum-Acevedo
(74) *Attorney, Agent, or Firm*—Hueschen and Sage

(57) ABSTRACT

The present invention relates to a pharmaceutical composition for administration by the nasal route of 17-β-oestradiol and norethisterone.

1 Claim, No Drawings

PHARMACEUTICAL COMPOSITIONS FOR NASAL DELIVERY OF OESTRADIOL AND NORETHISTERONE

The present invention relates to a pharmaceutical composition for administration by the nasal route of 17-β-oestradiol and norethisterone.

In women, oestrogen deficiency is responsible, in the short term, for climacteric disorders in 70% of women and, in the longer term, for osteoporosis in 30% of women and for an increased cardiovascular risk. Replacement treatment for the menopause continues to be faced with difficulties relating to compliance, which have been improved only in part by the pharmaceutical forms currently available.

Tablets, which are used widely, have the advantage of being well-established and simple, but their dosages lack the flexibility for adapting the dose. In addition, the first-pass effect in the intestine and the liver is responsible for their metabolic disadvantages. Transdermal systems enable the first-pass effect to be avoided but have significant drawbacks, such as poor local tolerance, the variability of the doses delivered and the difficulty of adapting doses. The nasal route allows systemic administration of an active ingredient while avoiding the first-pass effect in the liver and at the same time allowing ready adaptation of the administered doses by simple modification of the number of sprays.

The combination of 17-β-oestradiol and a progestagen in the same formulation is of particular interest for the following reasons: in women who have not undergone hysterectomy, the addition of a progestagen is essential for counteracting the proliferative effects of oestradiol on the endometrium and hence reducing the risk of hyperplasia and endometrial cancer. Combination in the same formulation, which ensures the effective intake of the progestagen, thereby guarantees good compliance and thus the effectiveness of the treatment.

The prior art is illustrated inter alia by the patent specification EP 0 349 091, which describes a formulation for the nasal administration to women of sex hormones, such as 17-β-oestradiol or progesterone, which formulation comprises a cyclodextrin, or by the patent specification EP 0 689 442, which describes a nasal composition comprising a protestagen and a cyclodextrin.

Those patent specifications provide a general description of nasal formulations comprising sex hormones and a cyclodextrin, but give no indication of the respective amounts of the constituents.

In those formulations, cyclodextrin, by complexing the hormones, allows them to be dissolved in aqueous medium in order to obtain a clear solution that can be used for administration by the nasal route. Such solutions need to be stable and, when administered by the nasal route, must allow the release of an amount of hormone that is sufficient for the therapeutic activity.

The problem to be solved is thus to provide a nasal formulation for the administration of oestradiol and norethisterone, containing a cyclodextrin, in which formulation the amount of cyclodextrin allows the two hormones to be complexed so as to obtain a solution that is stable and compatible with nasal physiology, allows good absorption of the hormones through the nasal mucosa and allows sufficient bioavailability of the hormones to produce the desired therapeutic effect.

The provision of a nasal formulation simultaneously comprising 17-β-oestradiol, a progestagen and a cyclodextrin and capable of meeting the therapeutic criteria has proved to be particularly complex.

Indeed, in such nasal formulations the absorption of sex hormones through the nasal mucosa is possible only if the hormones are dissolved beforehand in the aqueous solution to be administered.

On the other hand, it is essential in such solutions not only for the hormones to be present in the amounts necessary to achieve the desired therapeutic effect but also for the decomplexing to be as complete as possible at the time that they pass through the nasal mucosa, so as to avoid large amounts of complexed products being absorbed without any therapeutic effect.

Finally, it is also desirable in such formulations for the amount of cyclodextrin to be the smallest possible, so as to dispense with the side effects caused by that excipient.

Those hormones are sparingly soluble in aqueous medium and the use of complexing agents, such as cyclodextrin, renders possible their solubilisation. However, in nasal formulations containing two sex hormones, such as 17-β-oestradiol and a progestagen, the formation of complexes has proved not to be a simple addition of the amounts of complexing agents for each of the two active ingredients to be complexed. Surprisingly, it has been shown that the balance is achieved using a smaller amount of complexing agent.

On the other hand, the addition of a larger amount of complexing agent in relation to the minimum amount required to obtain a solution of the physically stable complexed products results in a loss in bioavailability of the two active ingredients and hence an increase in the doses of active ingredients necessary to obtain the desired therapeutic effect. It is essential, however, to reduce the amount of active ingredients to the minimum required to obtain the desired activity.

None of the prior art documents mentioned above enabled those difficulties to be foreseen and resolved.

More specifically, the present invention relates to a pharmaceutical composition in the form of an aqueous solution for administration, by the nasal route, of 17-β-oestradiol optionally in hydrated form, and norethisterone or norethisterone acetate, containing a partially methylated cyclodextrin, which composition is characterised in that it comprises:

oestradiol in an amount of from 2.2 to 2.8 mg per ml of solution, norethisterone or norethisterone acetate in an amount of from 3.5 to 4.5 mg per ml of solution, and partially methylated cyclodextrin in an amount of from 60 to 70 mg per ml of solution.

Preferably, the composition according to the invention will contain a randomly partially methylated cyclodextrin in which the average degree of substitution with methylated groups is approximately 1.7, hereinafter referred to as RAMEB.

In the composition according to the invention, oestradiol is preferably in hemihydrate form.

In the composition according to the invention, the progestagen will preferably be norethisterone.

The pH of the aqueous solution according to the invention will preferably be the physiological pH obtained by addition of a sodium chloride solution, enabling the isotonicity of the solution to be maintained, and optional adjustment to pH 6 to mimic nasal pH.

A preferred composition according to the invention is an aqueous solution for administration, by the nasal route, of 17-β-oestradiol and norethisterone (NET), containing RAMEB, characterised in that it contains:

2.5 mg of oestradiol hemihydrate per ml of solution,
3.93 mg of NET per ml of solution,
65 mg of RAMEB per ml of solution.

The pharmaceutical composition according to the invention will be administered by means of a device allowing administration by the nasal route that, with each spray, delivers the amount of active ingredients necessary to obtain the desired therapeutic effect. The nasal solution is preferably packaged in a bottle fitted with a metering pump that allows sprays of 70 µl to be dispensed. With each spray, the metering pump will deliver amounts of the nasal solution according to the invention that, per 70 µl, contain active ingredients in amounts of from 154 to 196 µg of oestradiol (hemihydrate) and from 245 to 315 µg of norethisterone.

EXAMPLE OF A PHARMACEUTICAL COMPOSITION ACCORDING TO THE INVENTION

Composition of a nasal aqueous solution according to the invention per 1 ml:

| | |
|---|---|
| Oestradiol hemihydrate | 2.5 mg |
| Norethisterone | 3.93 mg |
| RAMEB | 65 mg (6.5%) |
| sodium chloride | 9 mg |

The pH of the solution is 6.

This composition was clinically tested to determine the plasma concentrations of oestradiol and norethisterone compared with a solution containing 75 mg of RAMEB (7.5%) for the same amounts of active ingredients.

The curve below shows the effect of the concentration of RAMEB on the kinetics of oestradiol:

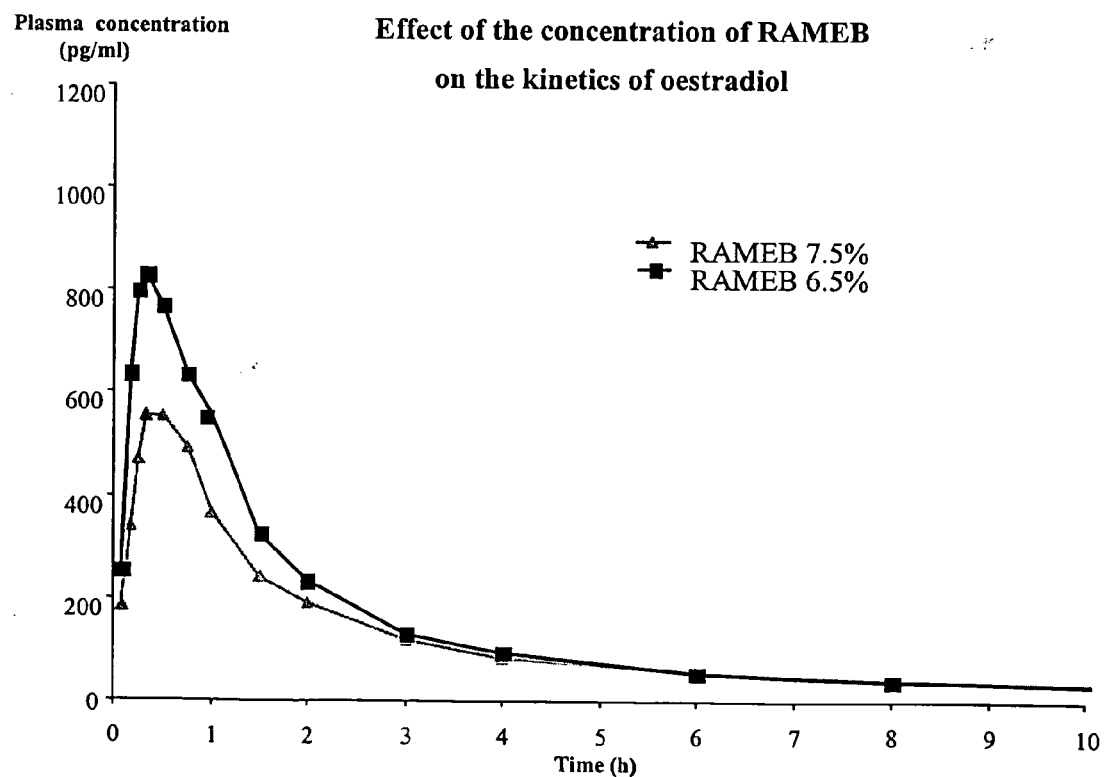

These results show that when the concentration of RAMEB increases (RAMEB 7.5%), a loss of bioavailability of approximately 30% is observed: the nasal solution according to the invention, which contains 6.5% RAMEB, allows a plasma concentration of oestradiol to be obtained that results in the desired therapeutic effect, whereas a nasal solution containing 7.5% of RAMEB results in such a loss of bioavailability that it cannot be contemplated for obtaining the desired therapeutic effect.

In order to achieve the desired bioavailability of oestradiol, a solution containing 7.5% of RAMEB with larger amounts of active ingredients was prepared: that solution proved to be unusable because in time the active ingredients reprecipitated.

Another nasal solution containing the same amounts of active ingredients but an amount of RAMEB equal to 55 mg per ml of solution was prepared: that solution proved unusable because in time the active ingredients reprecipitated.

Those results were also observed in relation to the kinetics of norethisterone.

It has thus been demonstrated through those examples that only aqueous compositions according to the invention make it possible to obtain not only solutions that are stable, without re-precipitation of the active ingredients, but also solutions that ensure maximum bioavailability of active ingredients leading to the desired therapeutic effect.

The invention claimed is:

1. An aqueous pharmaceutical composition formulated as a solution for nasal administration, which consists essentially of elements (a)–(d) on a per ml of solution basis:
   (a) 2.5 mg of oestradiol hemihydrate,
   (b) 3.93 mg of norethisterone,
   (c) 65 mg of a randomly partially methylated cyclodextrin with an average degree of substitution by methylated groups being approximately 1.7, and
   (d) 9 mg of sodium chloride, wherein the aqueous pharmaceutical composition has a pH of 6.

* * * * *